United States Patent [19]

Wojtech et al.

[11] Patent Number: 4,720,577
[45] Date of Patent: Jan. 19, 1988

[54] PROCESS FOR THE EXTRACTION OF CARBOXYLIC ACIDS FROM DILUTE AQUEOUS SOLUTIONS

[75] Inventors: Bernhard Wojtech, Bad Soden am Taunus; Walter Steppich, Wiesbaden; Dieter Freudenberger; Knut Riedel, both of Hofheim am Taunus, all of Fed. Rep. of Germany

[73] Assignee: Hoechst Aktiengesellschaft, Frankfurt am (Main), Fed. Rep. of Germany

[21] Appl. No.: 783,212

[22] Filed: Oct. 2, 1985

[30] Foreign Application Priority Data

Oct. 4, 1984 [DE] Fed. Rep. of Germany ....... 3436348

[51] Int. Cl.$^4$ .............................................. C07C 51/42
[52] U.S. Cl. .................................... 562/513; 562/580; 562/589; 562/600; 562/608; 562/609; 260/413; 260/419
[58] Field of Search ............... 562/513, 580, 589, 593, 562/606, 608, 609, 600; 260/413, 419

[56] References Cited

FOREIGN PATENT DOCUMENTS

| | | |
|---|---|---|
| 422073 | 11/1925 | Fed. Rep. of Germany . |
| 866969 | 5/1940 | France . |
| WO84/00364 | 2/1984 | PCT Int'l Appl. ................ 562/608 |
| 390185 | 3/1933 | United Kingdom ............... 562/608 |
| 168674 | 5/1965 | U.S.S.R. ............................. 562/608 |

OTHER PUBLICATIONS

Wardell et al., J. of Chem. & Engineering Data, vol. 23, No. 2, 1978, pp. 144–147.

*Primary Examiner*—Werren B. Lone
*Attorney, Agent, or Firm*—Curtis, Morris & Safford

[57] ABSTRACT

The invention relates to a process for the extraction of carboxylic acids from aqueous solutions with a carboxylic acid content below 8% by weight. A mixture of an aliphatic amine with a total carbon number of at least 10 and a phenol or naphthol is used as extracting agent. The molar ratio of phenol:amine or alkylated phenol:amine or naphthol:amine is in the range from 0.1:1 to around 1.1:1.

10 Claims, No Drawings

PROCESS FOR THE EXTRACTION OF CARBOXYLIC ACIDS FROM DILUTE AQUEOUS SOLUTIONS

The invention relates to a process for the extraction of carboxylic acids from aqueous solutions with a carboxylic acid content below 8% by weight.

Examples of solvents used for the separation of water-soluble carboxylic acids, in particular acetic acid, from relatively concentrated aqueous solutions by means of liquid-liquid extraction are esters, such as ethyl acetate or amyl acetate, or ketones, such as cyclohexanone or methyl isobutyl ketone. Conventional solvents of this type, whose extractive action is based on the improved solvation of the carboxylic acids in the organic medium ("physical extraction"), are not suitable for the separation from extremely dilute aqueous solutions (below 5% by weight of carboxylic acid) since the distribution coefficients D of the acids (D=acid concentration in the organic phase: acid concentration in the aqueous phase), with values of 1 or below, are too low for an economic process.

On the other hand, extraction agents which bond the carboxylic acids by attachment to form aggregates (complexes), i.e. by a chemical reaction ("chemical extraction"), can be used even in the case of very dilute solutions, e.g. waste waters. Extraction agents of this type contain functional polar groups with electron-donor properties (e.g. oxygen or nitrogen atoms), i.e. "basic" compounds which associate with the carboxylic acids by means of the acid (active) hydrogen of the carboxylic acids. According to U.S. Pat. No. 3,816,524 dialkyl-(alkyl)-phosphonates, alkyl-(dialkyl)-phosphinates, trialkylphosphine oxides and dialkylsulfoxides are, for example, suitable as polar extracting agents when diluted with various non-polar solvents. Of the extracting agents mentioned here trioctylphosphine oxide (TOPO) is the most effective.

With a D value around 3 for solutions in water without salt additive, the extraction power of the latter for acetic acid as the most important carboxylic acid to be extracted is markedly higher than in the case of the ketones and esters mentioned above. However, it is not yet high enough to reduce the extraction cost adequately. Thus, more than 8 theoretical stages are needed in counter-current operation to double the carboxylic acid concentration in the extract with 99% yield. The high costs for the relatively expensive TOPO have also to be borne in mind.

As an alternative to TOPO higher tertiary amines are proposed in the Journal of Chemical and Engineering Data, vol. 23, 144 (1978) because of the lower costs and higher distribution coefficients. In this connection, although the highest D values can be achieved with alcohols and chloroform as the diluting agent, in the case of the alcohols the tendency to esterification in the subsequent distillative separation of the acetic acid is disadvantageous and in the case of chloroform the environmental loading due to its water solubility and the corrosive action resuluting from elimination of HCl is disadvantageous. In addition, the volatility of the diluting agent is troublesome in the distillative separation of acetic acid. The use of ketones as diluting agents, which although less effective are also less reactive, is therefore advisable.

It has now been found that an inert extracting agent with an extremely high extracting power is obtained if a phenol or a naphthol is added to an aliphatic amine containing at least 10 C atoms.

The subject of the invention is a process for the extraction of carboxylic acids from aqueous solutions with a carboxylic acid content below 8% by weight, wherein a mixture of an aliphatic amine with a total carbon number of at least 10 and a phenol or naphthol is used as the extracting agent, the molar ratio of phenol:amine or naphthol:amine being in the range from 0.1:1 to around 1.1:1. The aliphatic amines may be primary, secondary or tertiary, and the alkyl group or groups has/have in total at least 10, preferably in total 20 to 50 C atoms, and may be straight-chain, cyclic or branched. Of the amines mentioned, particularly preferable are the tertiary ones such as trioctylamine or tridecylamine or mixtures of these.

Phenols and naphthols are used as the second component of the extraction agent. By preference alkylated phenols are used, the alkyl radical or radicals having 1 to 40, preferably in total 5 to 20 C atoms and being capable of being straight-chain or branched. The quantity of the phenol added should be chosen in a manner such that, apart from the quantity bound in the aggregate to the amine, no substantial amount of additional (unbound) phenol is present, whereas an excess of amine is not harmful because amine alone already associates with carboxylic acids, even if much more weakly. In the case of nonylphenol, which forms an aggregate with the trinonylamine, the proportion of phenol, for example, in the extracting agent should not substantially exceed 80% by weight. A proportion of 40 to 70% by weight of nonylphenol is advantageous, but even smaller proportions are still effective.

Suitable for extraction by the process according to the invention are water-soluble saturated and unsaturated carboxylic acids containing one or more carboxylic groups. The carboxylic acids may also be substituted, particularly with oxygen-containing functional groups. Examples of suitable acids are acetic acid, butyric acid, glycolic acid, lactic acid and malonic acid. The extraction of acetic acid is particularly important.

The aqueous solutions of these acids may also contain other dissolved organic or inorganic compounds and suspended particles provided these do not interfere with the extraction. A preceding extractive separation of interfering organic impurities is sometimes necessary. The extraction process according to the invention permits even the extraction of acids at very high dilution, especially from waste waters, e.g., from those having an acetic acid content around 1% by weight or below.

Because of the high boiling points of the components (e.g. nonylphenol, b.p.: ~300° C., trinonylamine, b.p.: ~350° C.) the preferred extraction agents consisting of alkylated phenols and tertiary amines have the advantage that lower-boiling carboxylic acids (e.g. acetic acid, b.p.: 118° C.) can be separated by distillation more easily.

The extraction can, for example, be carried out continuously in countercurrent in a multi-stage extractor, the extraction agent requirement, referred to the aqueous phase, being small because of the high distribution coefficient, so that the ratio of aqueous phase:organic phase (phase volume ratio) may be up to around 50:1. In this way a considerable enrichment of the carboxylic acid in the extract is possible. The high extraction power of the extracting agent, however, also permits single-stage extraction in an agitation vessel, the ratio of aqueous phase:organic phase being capable of being up to around 10:1.

The isolation of the carboxylic acids from the extract by the distillative route is advantageous, especially for low-boiling carboxylic acids. There is also the possibility of back extraction into water for higher temperatures. The back extraction of the carboxylic acid can also be carried out with alkali hydroxide solution with the formation of a salt.

The invention shall be explained using the following examples.

EXAMPLE 1

Samples of an aqueous acetic acid solution with an acid content of 1.4% by weight were equilibrated in shaking vessels at room temperature and with various phase-volume ratios, using, on the one hand, an extracting agent according to the invention consisting of an amine component mixed with nonylphenol in various proportions and, for comparison, using the amine component alone. A mixture of 50% by weight of tri-n-octylamine and 50% by weight of tri-n-decylamine were taken as the amine component. The distribution coefficients are given in Table 1 below.

TABLE 1

| Phase-volume ratio AP:OP | Extracting agent % by weight Amines | % by weight Nonylphenol | Acetic acid concentration % by weight OP | AP | Distribution coefficient |
|---|---|---|---|---|---|
| 1:1 | 100 | 0 | 0.8311 | 0.7331 | 1.1 |
| 2:1 | 100 | 0 | 1.0900 | 0.9556 | 1.1 |
| 1:1 | 60 | 40 | 1.342 | 0.0127 | 106 |
| 2:1 | 60 | 40 | 2.567 | 0.0576 | 45 |
| 2:1 | 50 | 50 | 2.580 | 0.270 | 96 |
| 2:1 | 40 | 60 | 2.490 | 0.0138 | 180 |
| 1:1 | 30 | 70 | 1.315 | 0.0043 | 306 |
| 2:1 | 30 | 70 | 2.556 | 0.0114 | 224 |
| 2:1 | 20 | 80 | 2.436 | 0.0757 | 32 |

AP = aqueous phase, OP = organic phase

EXAMPLE 2

Samples of aqueous solutions of various acids with an acid content of 5.0% by weight were equilibrated in shaking cylinders at room temperature and with a phase-volume ratio of aqueous phase (AP):organic phase (OP) of 1:1 or 2:1, on the one hand using an extraction agent according to the invention consisting of 60% by weight of tri-n-octylamine/tri-n-decylamine (1:1) and 40% by weight of nonylphenol, and, for comparison, with the mixture of tertiary amines alone. The distribution coefficients are shown in Table 2.

TABLE 2

| Acid | Phase-volume ratio AP:OP | Extracting agent % by weight Amines | % by weight Nonylphenol | Acid concentration % by weight OP | AP | Distribution coefficient |
|---|---|---|---|---|---|---|
| Butyric acid | 1:1 | 100 | 0 | 5.403 | 0.386 | 14 |
|  | 1:1 | 60 | 40 | 5.447 | 0.034 | 160 |
|  | 2:1 | 100 | 0 | 9.918 | 0.543 | 18 |
|  | 2:1 | 60 | 40 | 10.03 | 0.227 | 44 |
| Glycolic acid | 2:1 | 100 | 0 | 3.465 | 3.668 | 0,94 |
|  | 2:1 | 60 | 40 | 7.906 | 1.287 | 6,1 |
| Lactic acid | 1:1 | 100 | 0 | 3.018 | 1.427 | 2,1 |
|  | 1:1 | 60 | 40 | 4.605 | 0.045 | 102 |
| Malonic acid | 1:1 | 100 | 0 | 5.834 | 0.082 | 71 |
|  | 1:1 | 60 | 40 | 5.850 | <0.020 | >290 |

EXAMPLE 3

Samples of an aqueous acetic acid solution with an acid content of 1.4% by weight were equilibrated in shaking cylinders at room temperature and with a phase volume ratio of aqueous phase (AP):organic phase (OP) of 2:1 with an extracting agent which contained 40% by weight of phenol ($C_6H_5OH$) or $\beta$-naphthol mixed with 60% by weight of tri-n-octylamine/tri-n-decylamine (1:1). The distribution coefficients are listed in Table 3.

TABLE 3

| Extracting agent | Acetic acid concentration (% by weight) OP | AP | Distribution coefficient |
|---|---|---|---|
| Amines/phenol | 2.597 | 0.022 | 118 |
| Amines/$\beta$-naphthol | 2.530 | 0.016 | 158 |

EXAMPLE 4

An effluent water which contained 1.35% by weight of acetic acid was extracted in a single stage in an agitating container at room temperature and with a phase-volume ratio of 2:1 (aqueous phase:organic phase) using a mixture of 30% by weight of tri-n-octylamine/tri-n-decylamine (1:1) and 70% by weight of nonylphenol. The acetic acid concentration in an aqueous phase was 0.011% by weight and in the organic phase 2.47% by weight, which corresponds to an extraction yield of 99.3%. This experiment was repeated with the same waste water under the same conditions except only that 30% by weight of triisooctylamine was now taken as the tertiary amine. The extraction yield was 99.0% with an acetic acid concentration of 2.46% by weight in the aqueous phase and 0.012% by weight in the organic phase.

EXAMPLE 5

In a 6-stage mixing settler acetic acid was extracted from a waste water with an acetic acid content of 1.4% by weight in continuous countercurrent at room temperature with a mixture of 60% by weight of tri-n-octylamine/tri-n-decylamine (1:1) and 40% by weight of nonylphenol. The phase-volume ratio of aqueous phase:organic phase was 4:1. The acetic acid concentration in the aqueous phase at the end was 0.11% and in the organic phase 6.2%, corresponding to an extraction yield of 99.2%. Acetic acid was then distilled out of the organic phase at normal pressure until a sump temperature of 200° C. was reached. Under these circumstances 94% by weight of the acetic acid was recovered.

Reactions which are likely to produce waste water having a carboxylic acid content of less than 8 percent are generally reactions in which the acids are produced as a main product of by-product or in which the acids are used as solvents. For example, in the production of acetaldehyde from ethylene, acetic acid may be present in the waste water in amounts of about 2 percent. The extraction of the acid is desireable for the economic reason that it is a valuable product and for the ecological reason that a contaminent is removed from the unpurified waste water.

We claim:

1. A process for extracting a carboxylic acid from an aqueous solution, wherein the carboxylic acid is present in an aqueous solution at a concentration of less than 8% by weight, which comprises using as an extracting agent a mixture of an aliphatic amine having at least ten carbon atoms and phenol, phenol substituted by an alkyl group having a total of 1 to 40 carbon atoms, or a naphthol, wherein said extracting agent has a molar ratio of phenol:amine or said phenol substituted by an alkyl group:amine or naphthol:amine ranging from 0.1:1 to about 1.1:1.

2. The process as claimed in claim 1, wherein phenol substituted by an alkyl group having a total of 1 to 40 carbon atoms is used.

3. The process as claimed in claim 1, wherein a phenol substituted by an alkyl group having a total of 5 to 20 carbon atoms is used.

4. The process as claimed in claim 1, wherein the amine has a total of 20 to 50 carbon atoms.

5. The process as claimed in claim 2, wherein an amine having a total of 20 to 50 carbon atoms is used.

6. The process as claimed in claim 3, wherein an amine having a total of 20 to 50 carbon atoms is used.

7. The process as claimed in claim 1, wherein a naphthol is used.

8. The process as claimed in claim 1, wherein a phenol substituted by an alkyl group having a total of 1 to 40 carbon atoms is used and the amine is a tertiary amine.

9. The process as claimed in claim 1, wherein the carboxylic acid is acetic acid, glycolic acid, lactic acid or malonic acid.

10. The process as claimed in claim 9, wherein nonylphenol is used and the amine is tri-n-octylamine or tri-n-decylamine.

* * * * *